(12) United States Patent
Sapiens et al.

(10) Patent No.: US 12,364,390 B2
(45) Date of Patent: Jul. 22, 2025

(54) METHODS AND SYSTEMS FOR AUTOMATIC MEASUREMENTS OF OPTICAL SYSTEMS

(71) Applicant: EyeQue Inc., Newark, CA (US)

(72) Inventors: Noam Sapiens, Newark, CA (US); John Serri, Newark, CA (US)

(73) Assignee: EyeQue INC., Newark, CA (US)

( * ) Notice: Subject to any disclaimer, the term of this patent is extended or adjusted under 35 U.S.C. 154(b) by 665 days.

(21) Appl. No.: 17/739,933

(22) Filed: May 9, 2022

(65) Prior Publication Data

US 2022/0265141 A1 Aug. 25, 2022

Related U.S. Application Data

(63) Continuation-in-part of application No. 17/223,944, filed on Apr. 6, 2021, now Pat. No. 12,114,927, which is a continuation-in-part of application No. 16/809,482, filed on Mar. 4, 2020, now Pat. No. 11,503,997, which is a continuation-in-part of application No. 16/276,302, filed on Feb. 14, 2019, now Pat. No. 10,588,507, which is a continuation-in-part of application No. 15/491,557, filed on Apr. 19, 2017, now Pat. No. 10,206,566, application No. 17/739,933 is a continuation-in-part of application No. 16/176,631, filed on Oct. 31, 2018, now Pat. No. 11,432,718.

(60) Provisional application No. 62/409,276, filed on Oct. 17, 2016, provisional application No. 63/186,081, filed on May 8, 2021.

(51) Int. Cl.
*A61B 3/103* (2006.01)
*A61B 3/00* (2006.01)
*A61B 3/14* (2006.01)
*G06T 7/00* (2017.01)

(52) U.S. Cl.
CPC ............ *A61B 3/103* (2013.01); *A61B 3/0008* (2013.01); *A61B 3/14* (2013.01); *G06T 7/0014* (2013.01); *G06T 2207/30041* (2013.01)

(58) Field of Classification Search
CPC ......... A61B 3/103; A61B 3/0008; A61B 3/14; A61B 3/1035; A61B 3/0025; G06T 7/0014; G06T 2207/30041; G06T 2207/20084; G06T 7/0012
USPC ....................................................... 351/222
See application file for complete search history.

(56) References Cited

U.S. PATENT DOCUMENTS

| | | |
|---|---|---|
| 4,798,457 A | 1/1989 | Morohashi et al. |
| 5,104,214 A | 4/1992 | Sims |
| 5,113,287 A | 5/1992 | Nakayama |
| 7,742,244 B2 | 6/2010 | Liu et al. |
| 8,755,124 B2 | 6/2014 | Aschwanden et al. |

(Continued)

*Primary Examiner* — Mohammed A Hasan
(74) *Attorney, Agent, or Firm* — Steven A. Nielsen; NielsenPatents.com

(57) ABSTRACT

Disclosed embodiments include means and methods of automatically measuring numerous characteristics of an optical system, such as an eye. Measured or displayed optical properties may include but are not limited to. spherical power, cylinder and axis for astigmatism. Higher order optical aberrations may also be measured. Disclosed embodiments may be used to measure refraction for creating corrective lenses for eyeglasses and contact lenses. Measurements of higher order aberrations of an eye may be used for measuring enhanced correction, accommodation state and range.

5 Claims, 7 Drawing Sheets

(56) References Cited

U.S. PATENT DOCUMENTS

| | | |
|---|---|---|
| 2002/0118918 A1 | 8/2002 | Goldberg |
| 2008/0075380 A1* | 3/2008 | Dube .................... G01N 21/64 |
| | | 382/255 |
| 2012/0287398 A1 | 10/2012 | Baker et al. |
| 2013/0092816 A1 | 4/2013 | Barrett et al. |
| 2015/0320308 A1* | 11/2015 | Akiba .................... A61B 3/14 |
| | | 382/131 |
| 2016/0242644 A1 | 8/2016 | Winsor |
| 2017/0079526 A1* | 3/2017 | Tamura .................... A61B 3/09 |
| 2017/0139213 A1 | 5/2017 | Schmidtin |
| 2018/0303333 A1* | 10/2018 | Takeda .................. A61B 3/117 |
| 2019/0377236 A1 | 12/2019 | Jang et al. |

\* cited by examiner

METHODS AND SYSTEMS FOR AUTOMATIC MEASUREMENTS OF OPTICAL SYSTEMS

RELATED PATENT APPLICATION AND INCORPORATION OF REFERENCE

This is a utility application based upon and claims priority from U.S. patent application 63/186,081 filed on May 8, 2021. This application is a Continuation in Part (CIP) of U.S. patent application Ser. No. 16/685,017 filed on Nov. 15, 2019 which is a CIP of application Ser. No. 16/276,302 filed on Feb. 14, 2019, now U.S. Pat. No. 10,588,507 issued on Mar. 17, 2020, which is a CIP of application Ser. No. 15/491,557 filed on Apr. 19, 2017, now U.S. Pat. No. 10,206,566 issued on Feb. 19, 2019 which claims priority from patent application 62/409,276 filed on Oct. 17, 2016. The related applications and patents are incorporated herein by reference and made a part of this application. If any conflict arises between the disclosure of the inventions in this utility application and those in the related applications and/or patents, the disclosure in this utility application shall govern. Moreover, the inventor(s) incorporate herein by reference any and all patents, patent applications, and other documents hard copy or electronic, cited or referred to in this application and the related applications and patents.

COPYRIGHT AND TRADEMARK NOTICE

This application includes material which is subject or may be subject to copyright and/or trademark protection. The copyright and trademark owner(s) has no objection to the facsimile reproduction by any of the patent disclosure, as it appears in the Patent and Trademark Office files or records, but otherwise reserves all copyright and trademark rights whatsoever. Such trademarks may include "EyeQue."

BACKGROUND OF THE INVENTION

(1) Field of the Invention

The inventions generally relate to measuring properties of an optical system such as an eye. More particularly, the inventions relate to a number of new and novel optical measurement systems and methods sometimes using annular collimated beams, collection optics, beam shaping optics, illumination optics, beam splitters, array/symmetry detectors, beam expanders, demagnifiers, symmetry detectors, annulus masks, illumination optics, deformable lenses, symmetry-based images and balancing detectors and other components used in novel and useful configurations.

(2) Description of the Related Art

Commercially available autorefractors are usually cumbersome and expensive tools used by an optometrist or ophthalmologist. Some mobile versions of an autorefractor exist but these are still large and very expensive. Autorefractors of the related art are precision instruments that are extremely complex.

The disclosed embodiments may be implemented in a portable device that is relatively small, hand held, battery operated and inexpensive. The disclosed embodiments may be used by consumers directly.

BRIEF SUMMARIES OF THE INVENTIONS

A first embodiment compromises an annular collimated beam projected into the eye or optical system to be measured.

A second embodiment comprises an imaging system that images the focal plane of the eye or measured optical system.

A third embodiment comprises an imaging system of the focal plane of the eye or measured optical system through a deformable lens.

In a fourth embodiment, an eye or optical system is illuminated with a light that reflects off of the focal plane of the optical system, such as a reflection from the retina of an eye.

Figure 1A:
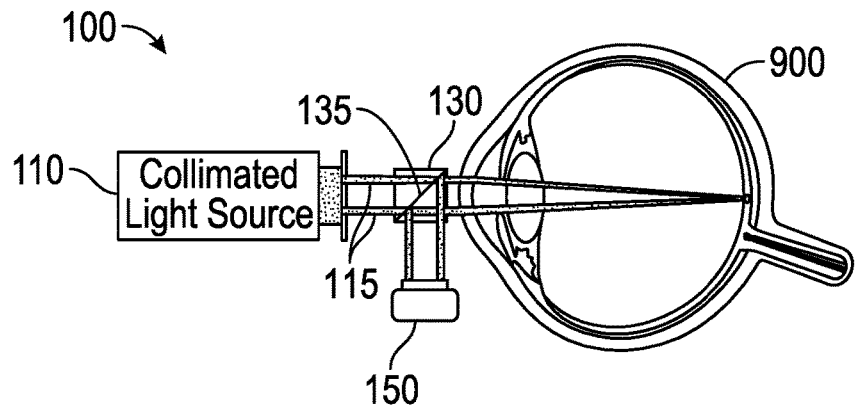
FIG. 1A is a sectional view of a disclosed embodiment

REFERENCE NUMERALS IN THE DRAWINGS 100 first embodiment in general
110 collimated light source
115 annular collimated beam
130 beam splitter
135 mirror disposed within beam splitter
150 array detector, such as a camera
160 collection optics
200 plurality of annulus shapes
210 input beam shape
220 emmetropic—no errors
230 myopic
240 hyperopic
250 astigmatic
255 axis
270 lens array
300 second embodiment
310 light source
320 beam shaping optics
330 illumination optics
340 objective
350 collection optics
360 annual mask
370 deformable lens
380 processing element
400 system to shape deformable lens
410 capture image
420 decision on whether image similar to object with criteria
430 object shape
440 criteria
450 follow algorithm and make change to deformable lens
460 record deformable lens parameters and report as output 470 scaling grid
500 through focus images
520 best focus algorithm
530 astigmatism parameter calculation algorithm
540 myopia parameter calculation algorithm
545 hyperopia parameter calculation algorithm
550 refraction correction parameters
900 optical system, such as an eye These and other aspects of the present invention will become apparent upon reading the following detailed description in conjunction with the associated drawings.

DETAILED DESCRIPTION OF EMBODIMENTS OF THE INVENTION

The following detailed description is directed to certain specific embodiments of the invention. However, the invention can be embodied in a multitude of different ways as defined and covered by the claims and their equivalents. In this description, reference is made to the drawings wherein like parts are designated with like numerals throughout.

Unless otherwise noted in this specification or in the claims, all of the terms used in the specification and the claims will have the meanings normally ascribed to these terms by workers in the art.

Unless the context clearly requires otherwise, throughout the description and the claims, the words "comprise," "comprising" and the like are to be construed in an inclusive sense as opposed to an exclusive or exhaustive sense; that is to say, in a sense of "including, but not limited to." Words using the singular or plural number also include the plural or singular number, respectively. Additionally, the words "herein," "above," "below," and words of similar import, when used in this application, shall refer to this application as a whole and not to any particular portions of this application.

Figure 1B:
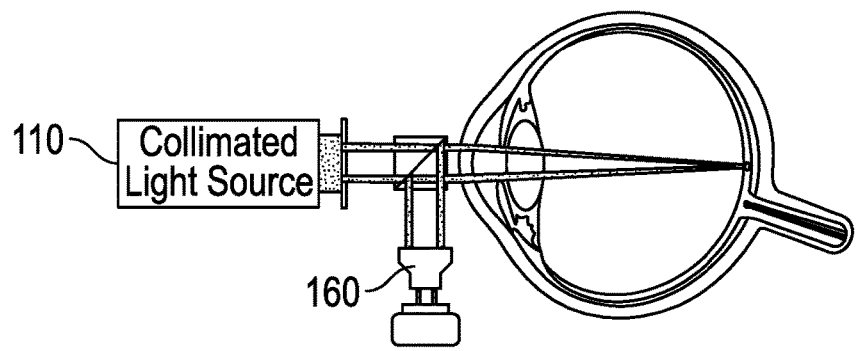
FIG. 1B is a sectional view of a second embodiment that includes collection optics

Referring to FIG. 1A, a disclosed embodiment may comprise an annular collimated beam is projected into the optical system to be measured. The beam is then either reflected from the focal surface of the optical system or travels through the optical system and captured by an array detector e.g. a camera. The beam could also traverse through collection optics, as shown in FIG. 1B, for a better capture of the image (e.g. reduction of the size of the image to match the array detector size). The captured image could then be analyzed to deduce the characteristics of the optical system. The analysis could be based on the calculations or on calibrations and a fit algorithm or sample images trained artificial intelligence system (e.g. neural network).

Figure 2:
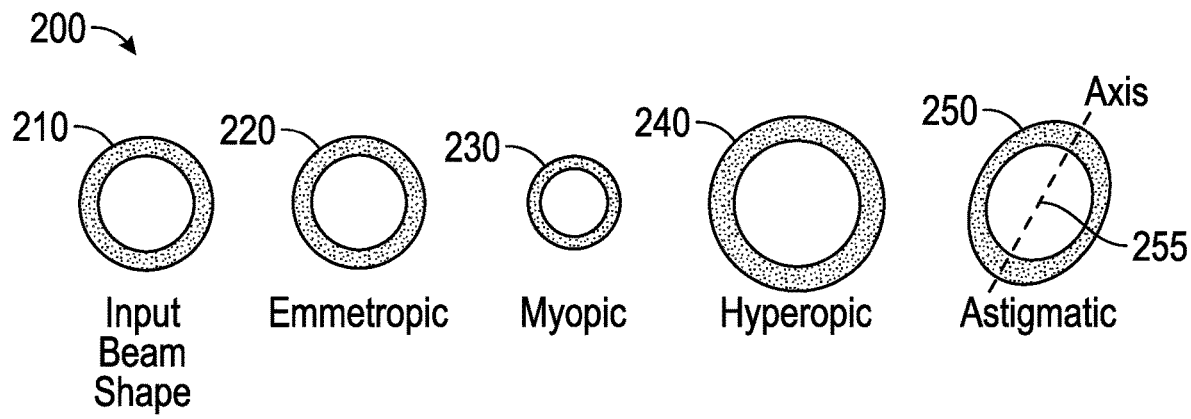
FIG. 2 depicts a plurality of annulus shapes

Referring to FIG. 2, assume an annulus illumination is incident into the optical system. The annulus may be made of parallel rays. In the case of an optical system with no refraction error the output beam will have the same annulus shape and size. A refraction error will induce a change in the annulus size and shape for a given distance from the measured optical system. FIG. 2 presents a schematic example of annulus shapes and sizes and the corresponding refraction errors.

An alternative analysis might include the incorporation of the calculation of the measured optical system point spread function (PSF). An optical system PSF is the system response to a point source illumination. The PSF includes information regarding system such as aberrations including defocus and astigmatism. The deformation of the annulus is indicative of the optical system PSF. In general, the output image will be a convolution of the input annulus with the transfer function representing the measured optical system.

The optical system characterization in terms of the transfer function could be deduced by deconvolution of the output image and the input image.

The input beam is generated by a light source. The light source could be for example a laser, an LED, a lamp or any other light source generating the required beam. The light generated could be conditioned through beam shaping optics, an illumination optics comprising for example of a collimator and an annular mask, or any other form of optical system to generate a collimated annular beam. The input beam could be of a wavelength that maximizes reflection/transmission in the measured optical system e.g. 750 nm-900 nm wavelength range for the human eye, in which the transmission is very high, and the retinal reflection is also very high. Furthermore, the wavelength could be chosen to minimize interference with the optical system operation e.g. IR wavelength for the human eye, so that the person cannot see the beam.

Figure 3:
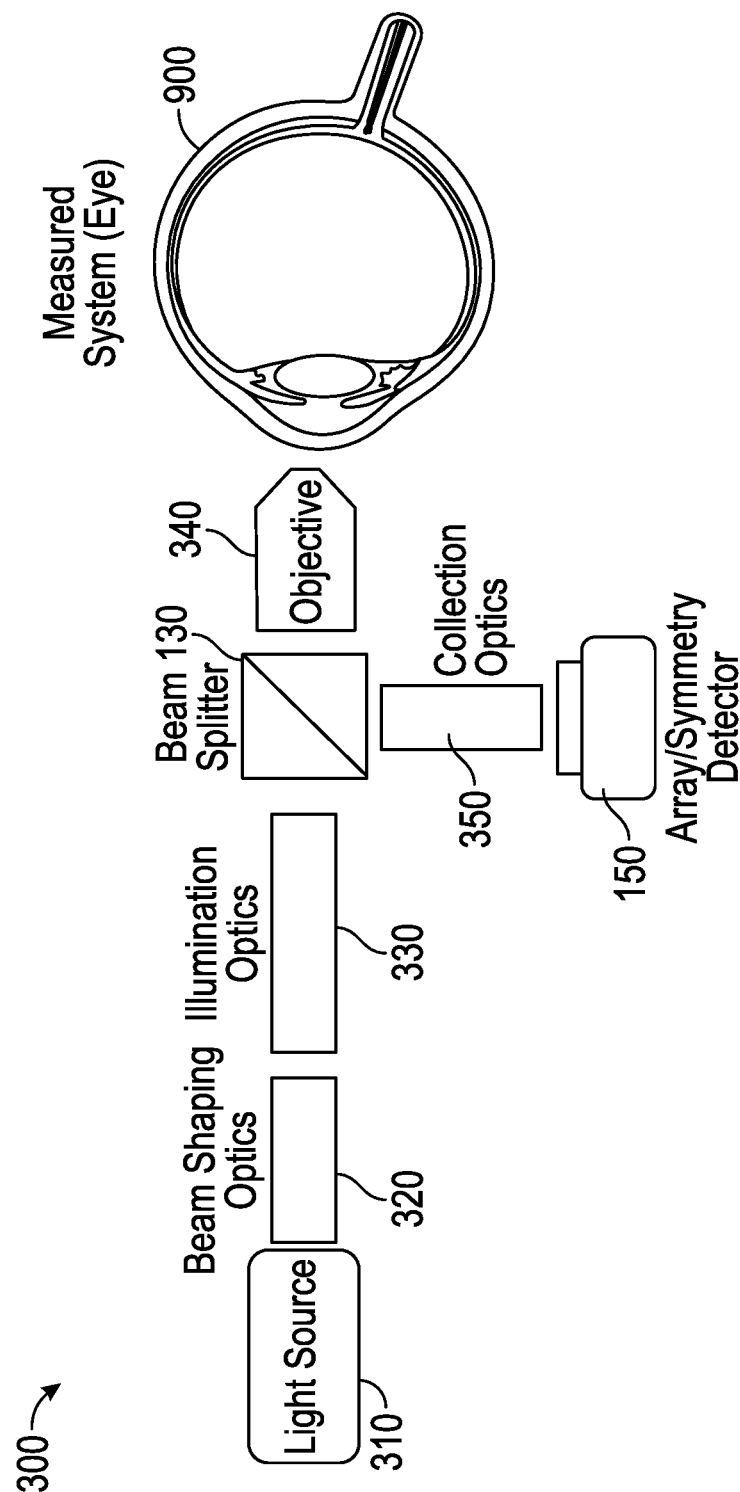
FIG. 3 depicts a sectional view of a disclosed embodiment

Referring to FIG. 3, another embodiment may involve an imaging system that images the focal plane of the measured optical system. A well-known object is projected on the optical system focal plane (examples include an annulus, a circular spot, a grid of dots, a grid of lines). The image deformation is related to the optical aberrations in the optical system. The measured optical system aberrations could be decoupled from the total sum of aberrations in the system by minimizing the aberrations of the device by optical design or by calibration which entails capturing images of well-known and characterized systems and matching them to the prospective aberrations. An AI system as described previously could also be used in this embodiment.

Figure 4:
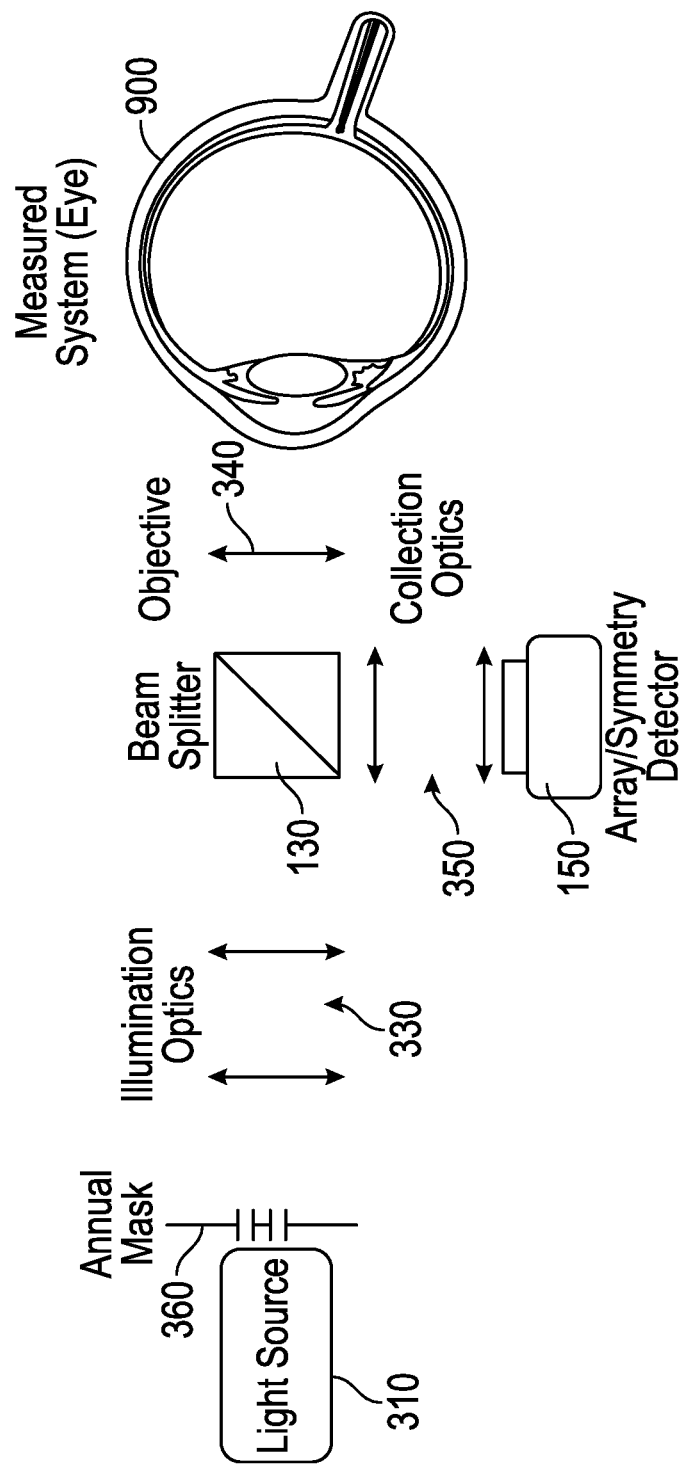
FIG. 4 depicts a sectional view of a disclosed embodiment

Referring to FIG. 4, an embodiment may include A light source, e.g. laser, lamp, LED, is incident upon a beam shaping optics that generates a well-known shape e.g. using a mask, a set of lenses, prisms or other optical components. The light shaped beam then goes through illumination optics that delivers the beam in a way as to provide the required characteristics for the imaging of the shaped beam onto the focal plane of the measured system e.g. the retina of an eye. The illumination optics may comprise for example an imaging lens, a beam expander, a demagnifier. The light then goes through a beam splitter that directs part of it into an objective. The objective may be an imaging lens, a microscope objective, a telescope objective, for example. The light then enters the measured system and is reflected back through the objective and the beam splitter onto collection optics. The collection optics may comprise an imaging lens, a beam expander, a demagnifier, for example. The purpose of which is to condition the image from the measured optical system onto the array detector, e.g. a camera or a quad detector (symmetry detector). In an embodiment of the invention the illumination optics, the objective, the collection optics or any combination thereof may not be present at all.

FIG. 4 presents an example embodiment with an annulus mask as the beam shaping optics, two imaging lenses (beam expander) as illumination optics, a single lens as the objective and two imaging lenses as collection optics.

Figure 5:
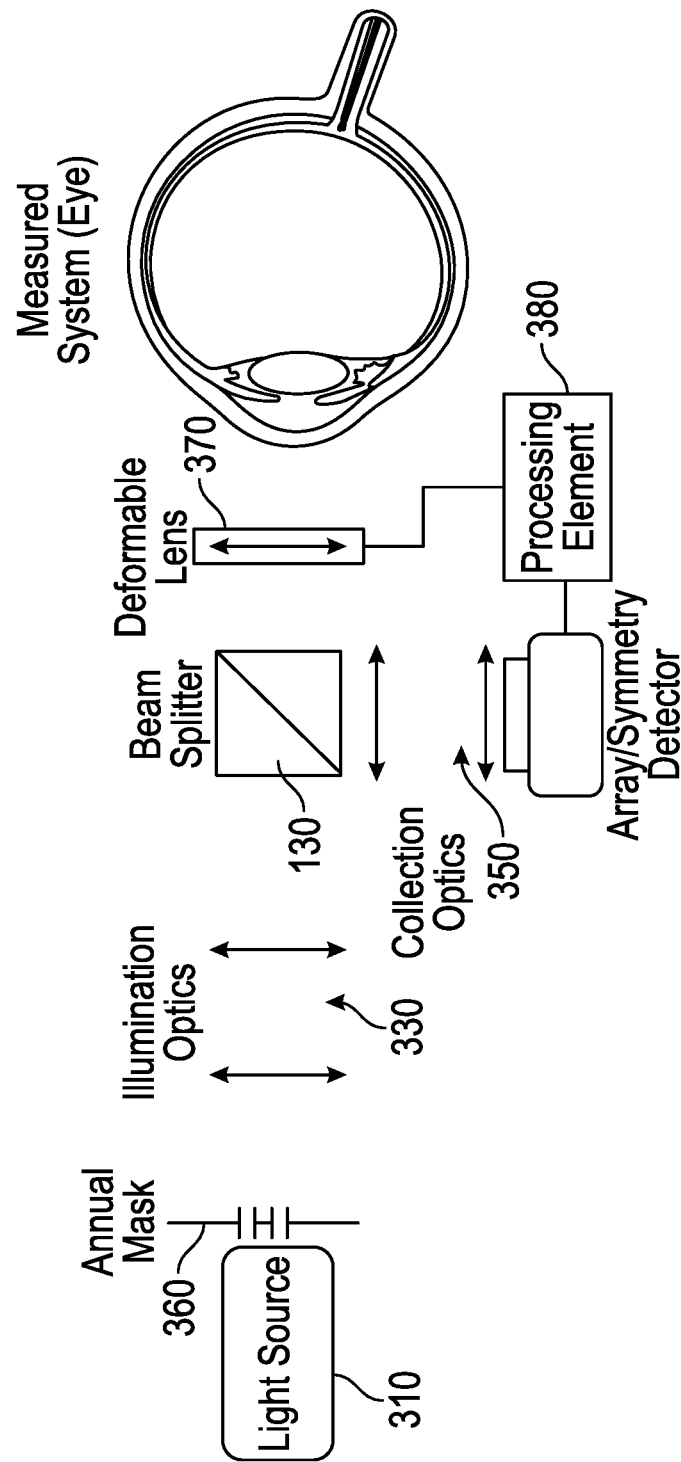
FIG. 5 depicts a sectional view of a disclosed embodiment

Referring to FIG. 5, another embodiment may include an imaging system of the focal plane of the measured optical system through a deformable/variable lens. A well-known object is projected on the optical system focal plane. The image of the object is captured by an array detector, e.g. camera.

The deformable lens would then be used to change the image until the measured image is returned to the original undisturbed or non-deformed object image. The refraction of the deformable lens would then be the refractive power required to correct for the measured system aberrations. Higher order aberrations could be achieved by allowing the variable lens to have higher order control and use the system in a feedback loop as shown in FIG. 6.

Figure 6:
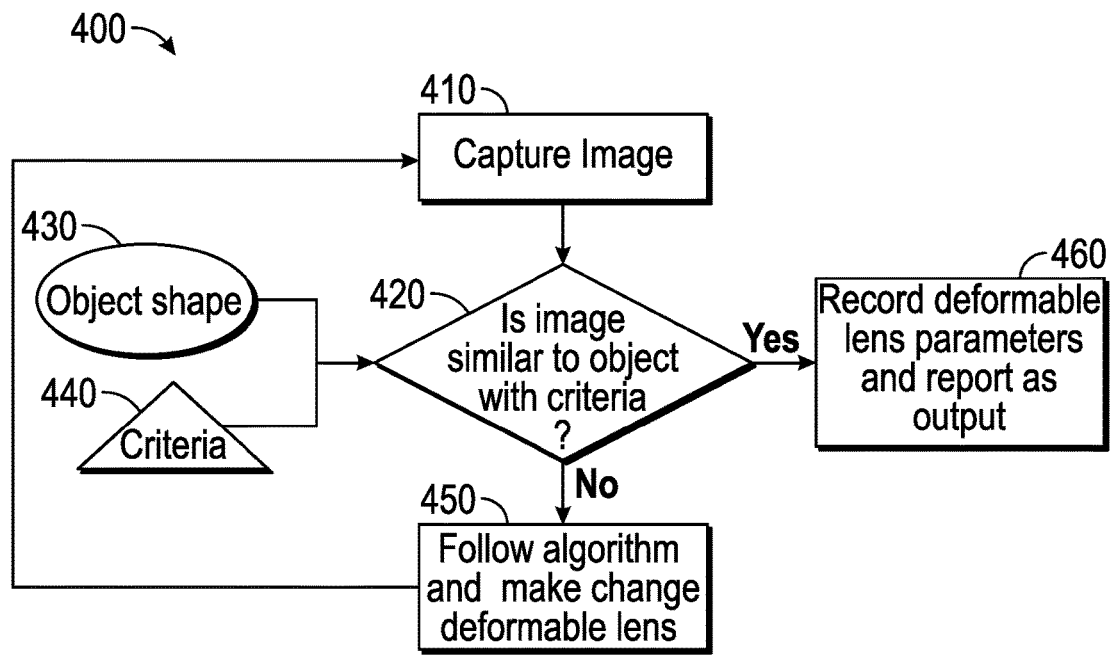
FIG. 6 depicts a series of steps for the fabrication of deformable lenes

Referring to FIG. 6, The feedback loop could be governed by a processing unit as in the example in FIG. 6. The captured image could be used as an input to an algorithm to deform the lens and achieve a final image that is similar enough to the given object as defined by comparison criteria.

Figure 7:
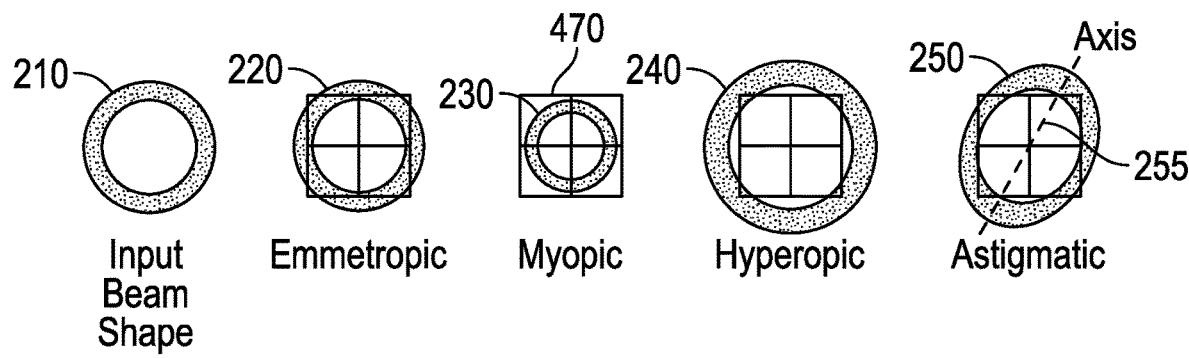
FIG. 7 depicts an implementation of the quad detector with an annulus input object.

Referring to FIG. 7, the measurement could also be achieved by a segmented detector e.g. quad cell detector. The measurement in this case would require a symmetry-based image and balancing the detector.

As an example, FIG. 7 presents an implementation of the quad detector with an annulus input object. The total power in the detector corresponds to the spherical component of the refraction error, while the asymmetry relates to the astigmatism.

Figure 8A:
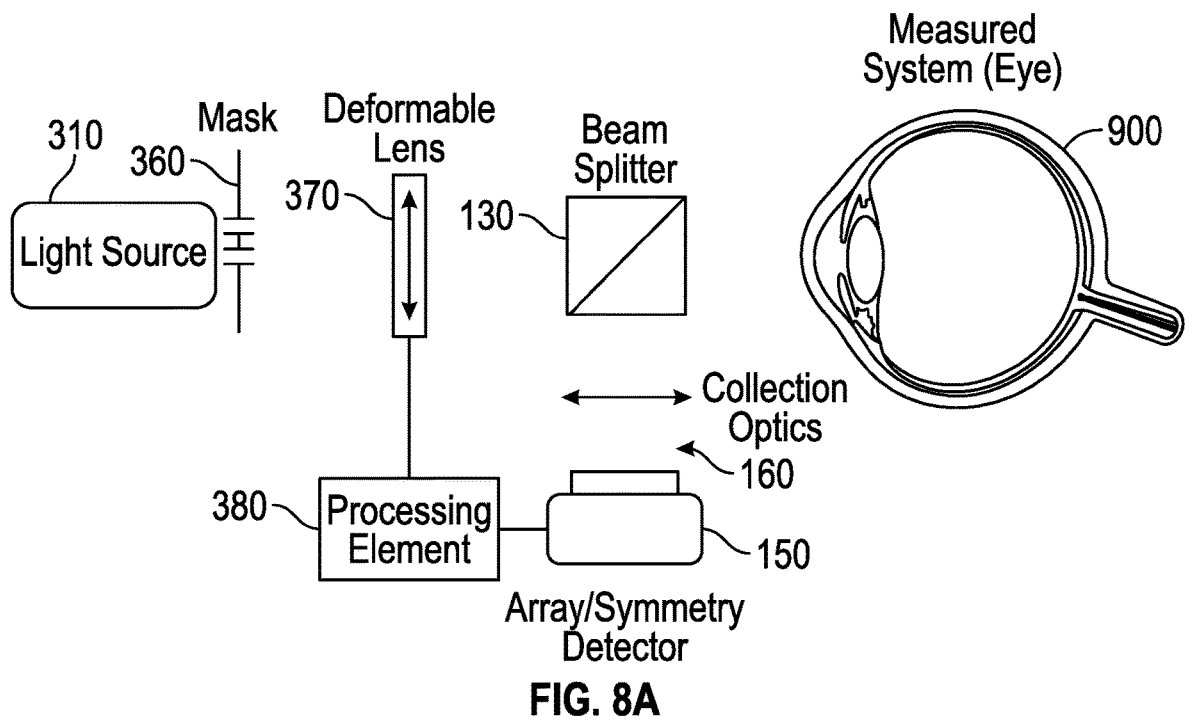
FIG. 8A depicts a sectional view of a disclosed embodiment
Figure 8B:
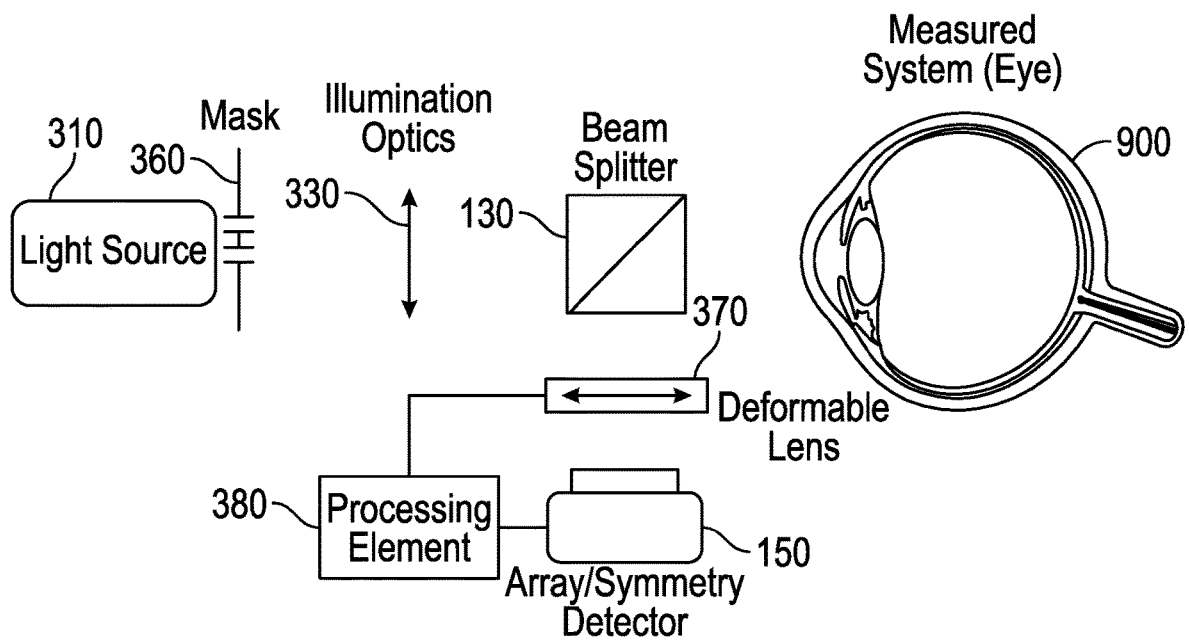
FIG. 8B depicts a sectional view of a disclosed embodiment

FIGS. 8A and 8B show examples of single pass embodiments of the invention, where the deformable lens is placed either in the illumination path where the correction is done in advance of the beam entering the measured optical system, pre-compensating for the system aberrations; or in the collection path of the system where it is compensating for the error in refraction in the measured optical system. While FIGS. 8A and 8B present a double pass solution of the invention, the correction amount in this case is "halved" as the light goes through the lens twice, which reduces the requirements on the deformable lens. This case also provides the most realistic form of correction for the human eye as the measured optical system, as the deformable lens effectively serves as corrective lens (e.g. glasses or contact lenses, depending on the distance of the deformable lens from the eye).

The most commercially available deformable lenses (if not all at this time) are spherical only. That is the control of the optical power of the lens is completely centrosymmetric. This yields aberration correction of the form of defocus only, higher orders are not corrected. It is still possible to perform the measurement in the above embodiments of the invention despite this limitation. In this case, in order to calculate higher order aberrations (especially for example astigmatism), a series of images or readings from the array detector should be taken while varying the focus of the deformable lens and analyzed to deduce the through focus dependence of the deformation. This information corresponds to the higher order aberrations. As an example, let us consider the case of astigmatism. FIG. 6 presents a calculation process based on a set of images of a through focus scan using the proposed system of FIG. 9.

Figure 9:
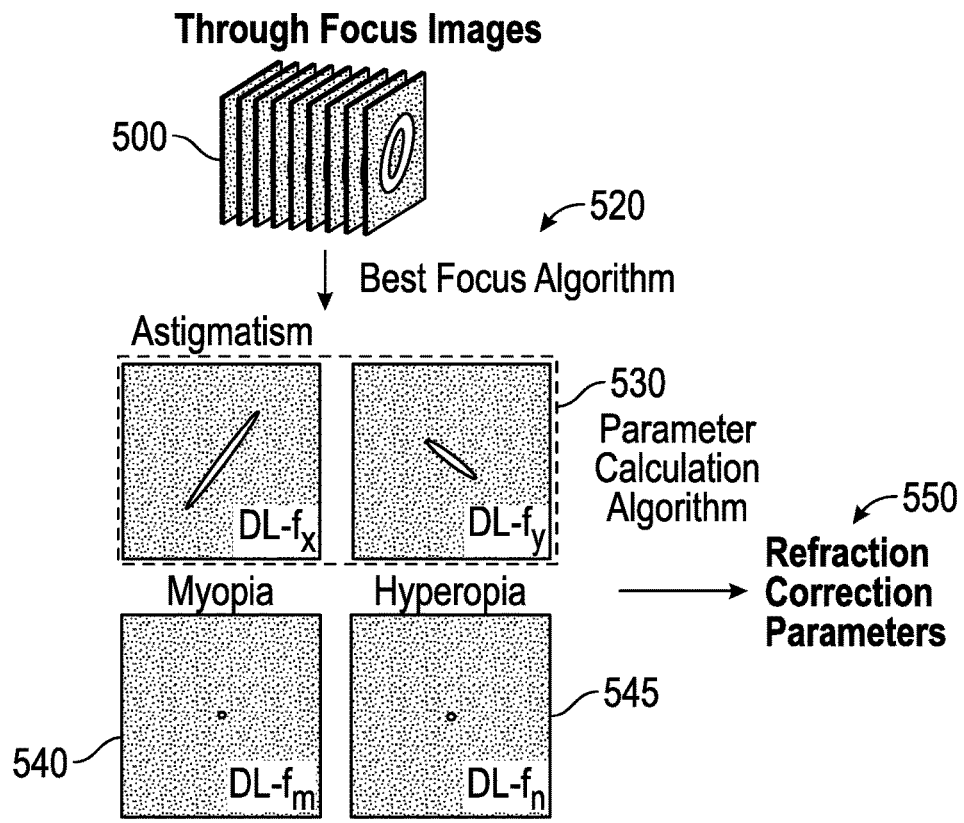
FIG. 9 depicts a best focus system

Referring to FIG. 9, as astigmatism essentially indicates different focal planes for two main directions, the best focus is calculated from the series of images and the focal lengths are recorded to calculate the astigmatic power. Furthermore, the directions are calculated based on the images to produce the axis of astigmatism (cylinder axis or just axis). This could also be performed in a quad detector setting as in FIG. 7 using a symmetry-based image as before and performing the analysis based on the different weighted meridians provided by the detector.

The deformable lens could be placed in multiple locations in the system corresponding to single pass or double pass correction.

Figure 10:
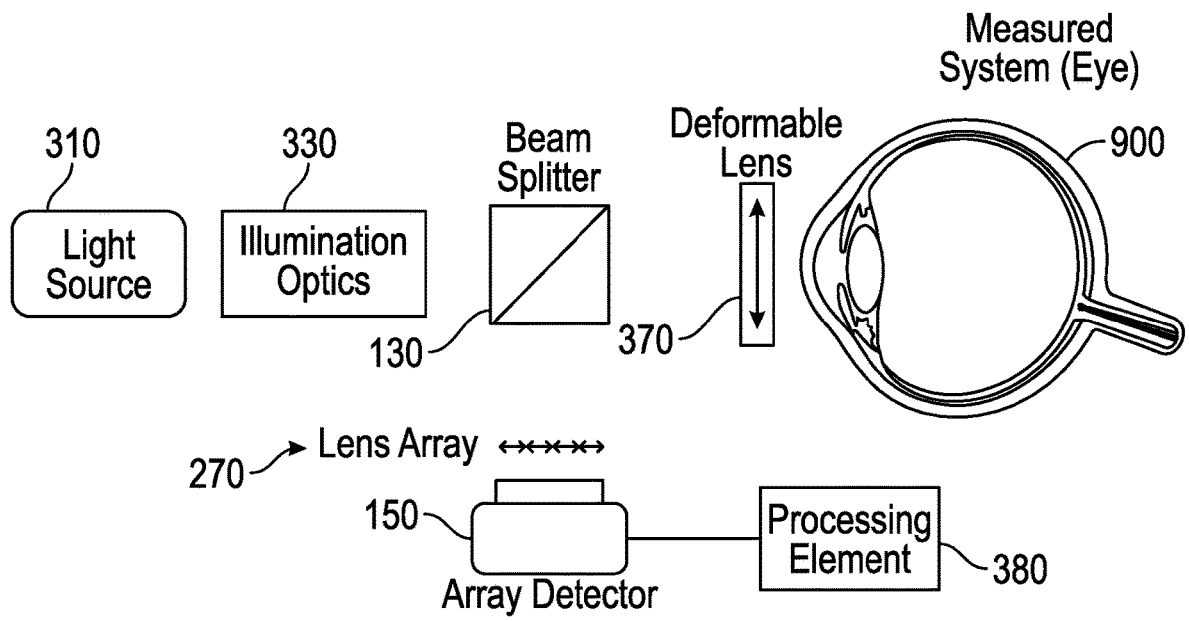
FIG. 10 depicts a system using a deformable lens and other components

FIG. 10 presents another embodiment, wherein the optical system is illuminated with a light that reflects off the focal plane of the system (e.g. reflection from the retina of an eye). The reflected light is then passed through a variable lens and a lenslet array and is incident on an array detector. The illumination system is for example a collimator. The variable lens is varied between images taken by the array detector. The offset of the focal points grid from an ideal grid is captured for each image. As the deviation for each point is taken for each variable lens value correlates to the overall aberration state of the optical system, a calculation could be made to find the aberration parameters such as defocus and astigmatism. Other higher order aberrations may also be computed.

An example of such calculation is given henceforth:

The power of the deformable lens is captured for each incident where the spot of any lenslet corresponds to either the x or y coordinates of the center of the segment. This in turn is used to calculate the Zernike polynomials that fit these coordinates. The Zernike polynomials then can be used to deduce the aberration characterizing the optical system.

The above detailed description of embodiments of the invention is not intended to be exhaustive or to limit the invention to the precise form disclosed above. While specific embodiments of, and examples for, the invention are described above for illustrative purposes, various equivalent modifications are possible within the scope of the invention, as those skilled in the relevant art will recognize. For example, while steps are presented in a given order, alternative embodiments may perform routines having steps in a different order. The teachings of the invention provided herein can be applied to other systems, not only the systems described herein. The various embodiments described herein can be combined to provide further embodiments. These and other changes can be made to the invention in light of the detailed description.

All the above references and U.S. patents and applications are incorporated herein by reference. Aspects of the invention can be modified, if necessary, to employ the systems, functions and concepts of the various patents and applications described above to provide yet further embodiments of the invention.

These and other changes can be made to the invention in light of the above detailed description. In general, the terms used in the following claims, should not be construed to limit the invention to the specific embodiments disclosed in the specification, unless the above detailed description explicitly defines such terms. Accordingly, the actual scope of the invention encompasses the disclosed embodiments and all equivalent ways of practicing or implementing the invention under the claims.

While certain aspects of the invention are presented below in certain claim forms, the inventors contemplate the various aspects of the invention in any number of claim forms.

Disclosed embodiments may include the following items:
1. A method of measuring properties of an optical system, the method comprising the steps of:
    a) projecting an annular collimated beam to the optical system;
    b) using collection optics to capture the annular collimated beam reflected from the optical system to obtain a reflected annular image;
    c) using an analysis of the reflected annular image to derive the properties of the optical system.
2. The method of item 1 using an artificial neural network to derive the properties of the optical system by analysis of the reflected annular image.

3. The method of item 1 using an artificial neural network to derive the properties of the optical system by analysis of the reflected annular image as compared to sample annular images.
4. The method of item 1 wherein the annular collimated beam is projected through the collection optics before reaching the optical system.
5. The method of item 1 further including the step of using a point spread function to derive the properties of the optical system.
6. The method of item 1 further including the step of using a fit algorithm upon the reflected annular image to derive the properties of the optical system.
7. The method of item 1 further including the step of using calibrations from sample annular images to derive the properties of the optical system.
8. The method of item 1 further including the step of mapping sample annular images having known optical errors to the reflected annular image to derive the properties of the optical system.
9. The method of item 1 wherein a point source beam is used in projecting the annular collimated beam.
10. The method of item 1 wherein and LED is used in projecting the annular collimated beam.
11. A system of measuring properties of an optical system, the system comprising:
    a) an annular collimated beam projected to the optical system;
    b) reflection optics receiving the annual collimated beam as reflected form the optical system;
    c) an analysis of the reflected annular image used to derive the properties of the optical system.
12. The system of item 11 further including an artificial neural network to derive the properties of the optical system by analysis of the reflected annular image.
13. The system of item 11 further including sample annular images used in comparison with the reflected annular image to derive the properties of the optical system.
14. The system of item 11 wherein the annular collimated beam is projected through the collection optics before reaching the optical system.
15. The system of item 11 further including a point source beam used in projecting the annular collimated beam.
16. The system of item 11 further including an LED used in projecting the annular collimated beam.
17. A method of measuring properties of an optical system, the system comprising the steps of:
    a) projecting an illumination to form an annulus input wherein the annulus input is projected to the optical system;
    b) using collection optics to capture a reflection of the annulus input from the optical system to obtain an annulus output image;
    c) obtaining a transfer function to represent the properties of the optical system, the transfer function being derived by deconvolution of the annulus output as compared to the annulus input.
18. The method of item 17 wherein the annulus input is projected through the collection optics before reaching the optical system.
19. The method of item 17 further including the step of using a point spread function to derive the transfer function.
20. The method of item 17 wherein the point source illumination takes the form of a laser.
21. The method of item 17 further including the step of conditioning the point source illumination by use beam shaping optics.
22. The method of item 17 further including the step of using collimator and annular mask to generate a collimated annular beam that is projected to the optical system.
23. The method of item 22 further including the step of using a collimated annular beam comprising a wavelength in the range of 750 nm to 900 nm.
24. The method of item 23 further including the step of using a collimated annular beam having a wavelength range selected to minimize interference with the optical system such that the collimated annular beam is not perceived by the optical system.
25. A method of measuring properties of an optical system, the method comprising the steps of:
    a) projecting a predefined image upon a focal plane of the optical system;
    b) using collection optics to obtain a reflected image from the reflection of the predefined image reflected from the focal plane;
    c) using an array/symmetry detector to accept the reflected image from the collection optics;
    d) using the array/symmetry detector to derive the properties of the optical system.
26. The method of item 25 further including the steps of producing the predefined image upon the focal plane by use of a light source, beam shaping optics, illumination optics, a beam splitter and objective.
27. The method of item 26 further including the step of constructing the illumination optics by use of an imaging lens, a beam expander and a demagnifier.
28. The method of item 26 further including the step of using an imaging lens for the objective.
29. The method of item 25 further including the step of using the collection optics to condition the reflected image for use by the array/symmetry detector.
30. The method of item 26 further including the step of using an annulus mask as a beam shaping optic.
31. The method of item 26 further including the step of using a plurality of imaging lenses as collection optics.
32. A method of measuring properties of an optical system, the method comprising the steps of:
    a) projecting a predefined image through a deformable lens with a resulting image projected upon a focal plane of the optical system;
    b) using an array detector to measure an image reflected form the optical system;
    c) using the deformable lens to reshape the resulting image projected to the focal plane until the reflected image measured by the array detector comports with the predefined image;
    d) using the final refraction of the deformable lens as the derived optical system properties.
33. The method of item 32 further including the step of using a processing element, the processing element in electronic communication with the array detector and deformable lens.
34. The method of item 33 further including the step of using a feedback loop to adjust the deformable lens to a final refraction.
35. The method of item 34 further including the step of using a segmented detector in analyzing the images obtained by the array detector.

36. The method of item 32 using the deformable lens positioned to achieve a single pass configuration, wherein the reflected image only passes through the deformable lens.

37. A method of measuring properties of an optical system, the method comprising the steps of:
   a) projecting a predefined image through illumination optics and then a deformable lens with a resulting image projected upon a focal plane of the optical system;
   b) an image reflected from the optical system is passed through a variable lens and a lenslet array with the variable lens and lenslet array incident to an array detector;
   c) the variable lens is varied between images captured by the array detector
   d) an offset of a focal points grid from a predefined ideal grid is captured in each image;
   e) as the deviation for each focal point is obtained for each variable lens value, defocus and astigmatism of the optical system may be derived.

38. The method of item 37 further including the step of recording the power of the deformable lens for each incident where the spot of any lenslet corresponds to either the x or y coordinates of the center of the segment with the recorded information used to calculate Zernike polynomials that fit the coordinates with the Zernike polynomials used to derive the properties of the optical system.

39. The method of item 37 further including the step where a collimator is used as part of the illumination optics.

40. The method of item 37 further including the step of using a processing element in electronic communication with the array detector and deformable lens.

41. A system of measuring properties of an optical system, the system comprising:
   a) a predefined image projected through a deformable lens with a resulting image projected upon a focal plane of the optical system;
   b) an array detector used to measure an image reflected from the optical system;
   c) the deformable lens used to reshape the resulting image projected to the focal plane until the reflected image measured by the array detector comports with the predefined image;
   d) the final refraction of the deformable lens used as the derived optical system properties.

42. The system of item 41 further including a processing element, the processing element in electronic communication with the array detector and deformable lens.

43. The system of item 41 further including a feedback loop used to adjust the deformable lens to a final refraction.

44. The system of item 41 further including a segmented detector used in analyzing the images obtained by the array detector.

45. The system of item 41 wherein the deformable lens positioned to achieve a single pass configuration, wherein the reflected image passes only through the deformable lens.

What is claimed is:

1. A method of measuring properties of an optical system, the method comprising the steps of:
   a) projecting a predefined image through a deformable lens with a resulting image projected upon a focal plane of the optical system;
   b) using an array detector to measure an image reflected form the optical system;
   c) using the deformable lens to reshape the resulting image projected to the focal plane until the reflected image measured by the array detector comports with the predefined image;
   d) using the final refraction of the deformable lens as the derived optical system properties.

2. The method of claim 1 further including the step of using a processing element, the processing element in electronic communication with the array detector and deformable lens.

3. The method of claim 2 further including the step of using a feedback loop to adjust the deformable lens to a final refraction.

4. The method of claim 3 further including the step of using a segmented detector in analyzing the images obtained by the array detector.

5. The method of claim 1 using the deformable lens positioned to achieve a single pass configuration, wherein the reflected image only passes through the deformable lens.

* * * * *